US011213483B2

(12) United States Patent
Chowdhury (10) Patent No.: US 11,213,483 B2
(45) Date of Patent: *Jan. 4, 2022

(54) IMPLANTABLE SOLID DOSAGE FORM

(71) Applicant: NDM TECHNOLOGIES LIMITED, Loughborough (GB)

(72) Inventor: Dewan Fazlul Hoque Chowdhury, Loughborough (GB)

(73) Assignee: NDM TECHNOLOGIES LIMITED, Loughborough (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/506,850

(22) Filed: Jul. 9, 2019

(65) Prior Publication Data

US 2019/0328655 A1   Oct. 31, 2019

Related U.S. Application Data

(63) Continuation of application No. 15/027,296, filed as application No. PCT/GB2014/052985 on Oct. 2, 2014, now Pat. No. 10,434,060.

(30) Foreign Application Priority Data

Oct. 5, 2013  (GB) ..................................... 1317641
Jul. 25, 2014 (GB) ..................................... 1413253

(51) Int. Cl.
| | | |
|---|---|---|
| A61K 9/00 | (2006.01) | |
| B29C 48/09 | (2019.01) | |
| A61K 38/17 | (2006.01) | |
| A61M 37/00 | (2006.01) | |
| A61M 5/32 | (2006.01) | |
| B29C 39/02 | (2006.01) | |
| B29C 41/02 | (2006.01) | |
| B29C 43/02 | (2006.01) | |
| B29C 43/36 | (2006.01) | |
| B29K 1/00 | (2006.01) | |
| B29K 105/00 | (2006.01) | |
| B29L 31/00 | (2006.01) | |

(52) U.S. Cl.
CPC ........ A61K 9/0024 (2013.01); A61K 38/1709 (2013.01); A61M 5/32 (2013.01); A61M 37/0015 (2013.01); A61M 37/0069 (2013.01); B29C 39/028 (2013.01); B29C 41/02 (2013.01); B29C 43/027 (2013.01); B29C 43/36 (2013.01); B29C 48/09 (2019.02); A61M 2207/00 (2013.01); B29C 2043/029 (2013.01); B29K 2001/00 (2013.01); B29K 2001/08 (2013.01); B29K 2105/0035 (2013.01); B29K 2995/006 (2013.01); B29L 2031/753 (2013.01)

(58) Field of Classification Search
None
See application file for complete search history.

(56) References Cited

U.S. PATENT DOCUMENTS

| | | | | |
|---|---|---|---|---|
| 4,753,636 A | * | 6/1988 | Free ................ | A61B 17/32093 604/115 |
| 5,409,662 A | * | 4/1995 | Hirai ...................... | B30B 11/26 419/67 |
| 6,001,385 A | * | 12/1999 | Van De Wijdeven ...... | A61K 9/0024 424/422 |
| 10,434,060 B2 | * | 10/2019 | Chowdhury ............ | B29C 43/36 |
| 2010/0080839 A1 | * | 4/2010 | Van De Wijdeven ...... | A61K 9/1652 424/426 |
| 2010/0119570 A1 | * | 5/2010 | Potter .................... | A61K 39/05 424/422 |
| 2010/0158800 A1 | | 6/2010 | Mckay | |
| 2010/0204678 A1 | | 8/2010 | Imran | |
| 2011/0313348 A1 | | 12/2011 | Potter et al. | |
| 2013/0123707 A1 | | 5/2013 | Determan et al. | |
| 2014/0066842 A1 | * | 3/2014 | Zhang .................... | A61P 23/02 604/46 |

FOREIGN PATENT DOCUMENTS

| | | |
|---|---|---|
| EP | 0049068 A1 | 4/1982 |
| EP | 2153863 A1 | 2/2010 |
| GB | 1316998 A | 5/1973 |
| GB | 2154138 A | 9/1985 |
| GB | 2414675 A | 12/2005 |
| JP | S62-70316 A | 3/1987 |
| JP | 2011-508611 A | 3/2011 |
| WO | 1984/00304 A1 | 2/1984 |
| WO | 1996/09070 A1 | 3/1996 |
| WO | 2005/123173 A1 | 12/2005 |
| WO | 2008/105663 A1 | 9/2008 |
| WO | 2012/020261 A2 | 2/2012 |
| WO | 2012/122162 A1 | 9/2012 |
| WO | 2012/154986 A1 | 11/2012 |

OTHER PUBLICATIONS

Gill et al., Coated microneedles for transdermal delivery. J Control Release. Feb. 12, 2007;117(2):227-37.

* cited by examiner

*Primary Examiner* — Tigabu Kassa
*Assistant Examiner* — Ivan A Greene
(74) *Attorney, Agent, or Firm* — McCarter & English, LLP; Steven G. Davis; Mei Bai (57) ABSTRACT

A solid dose for insertion into the skin of a patient wherein the solid dose has a hollow core. There is also provided a solid dose carrier, a device, a method of manufacturing the solid dose and a method of delivering a solid dose transdermally to a human or animal.

15 Claims, 6 Drawing Sheets

Figure 1

Skin

IMPLANTABLE SOLID DOSAGE FORM

CROSS-REFERENCE TO RELATED APPLICATIONS

This application is a continuation of U.S. application Ser. No. 15/027,296, filed on Apr. 5, 2016, which is a 35 U.S.C. § 371 national stage filing of International Application No. PCT/GB2014/052985, filed on Oct. 2, 2014, which claims the benefit of United Kingdom Patent Application No. 1317641.7, filed on Oct. 5, 2013, and United Kingdom Patent Application No. 1413253.4, filed on Jul. 25, 2014. The contents of each of the foregoing applications are incorporated herein by reference in their entirety.

The invention relates to the transdermal delivery of drugs to a patient. In particular, it relates to the delivery of a solid dose into the skin of a patient.

Syringes and needles have been widely used to deliver drugs to a patient. The patient may be human or animal. This requires skilled personnel to deliver the drug and there is a period of time associated with the delivery of drugs using such a technique during which the device must be resident in the skin to allow complete delivery of the dose inside the to skin. Microneedle technologies allow the delivery of a smaller mass of drug carried by one or more needles into the skin. However the microneedle technology also faces the issue of prolonged skin insertion, which is required for the drug to dissolve into the skin from the surface of the needle as the drug is adhered or coated to the needle, or the needle is produced from the drug.

Glide Pharma (see applications US 2011/0313348, and US 2010/0119570) have developed a device that allows the Instant delivery of a solid dose into the skin. However the solid dose must have the requisite properties to maintain tip sharpness and hardness to be able to penetrate the skin. The drug pellet is directly inserted into the skin using a device described as having a pointed or chisel shaped tip, which is forced into the skin using a spring loaded mechanism to provide the requisite insertion force such that the tip of the drug pellet is able to overcame the mechanical barrier posed by the drug.

However, most drugs do not lend themselves to the qualities required for direct skin insertion, and the use of large amounts of polymers and carbohydrate based excipients to enhance the mechanical strength of said drug pellets act to limit the drug loading reducing its practical utility. This is a major impediment of such a device.

WO2006/082439 describes a device with a skin piercing projectile which first enters the skin followed by the solid drug formulation immediately behind, as an integrated unit, whereby the skin projectile is a part of the solid dose, albeit an inert part of it with the function of piercing the skin and eventually dissolving and being absorbed into the body. WO2012/098356 describes a means of first cutting the skin using a blade, followed by the insertion of the drug into the skin. This is essentially identical in principle to the disclosure in WO2012/035334, filed by the present applicant, describing a device that first creates an opening in the skin followed by the insertion of the drug.

Other devices such as that described in PCT/US2000/015312 describe the loading of drugs in a slit built into the tip region of the needle, or in another case to the side of a needle with a cavity that had been etched out to hold the drug. However, given that the drug must be held within that cavity and must dissolve in the skin to be released into the skin, it does not provide for instant delivery, depth and duration of skin insertion which will ultimately affect the extent of drug absorption.

It is preferable to have a device that allows for skin insertion of a solid dose without the need for the drug to have properties which have high mechanical strength and properties that lend the drug to being inserted directly into the skin, and one that allows instant skin delivery of a solid dose. It would be preferable to be able to insert drug doses into the skin using a single motion that may or may not require an insertion rod to deposit the solid dose into the skin, and one that may or may not require additional mechanical force from a supplementary device or mechanism such as a spring or pneumatic force for example.

Furthermore it would be preferable to be able to deliver a solid dose with an enlarged surface area that enhances the speed of dissolution of the solid drug once inside the skin and in contact with the interstitial fluid or micro circulation in the skin, or one that provides a greater degree of control and consistency over sustained drug release profiles.

This invention describes a solid dose that is seated around a carrier with a hollow core through which the carrier protrudes with a portion in the distal region of the carrier which is able to pierce the skin to remove the barrier to skin-insertion of a solid dose, thereby allowing for the dose to be delivered with low force, to a defined depth and instantly without the need for any residence time of the carrier inside the skin once the solid dose has been inserted.

By "defined depth" the skilled person would understand this term to mean at a depth of the skin which would allow release of the 'active ingredient', and/or absorption of the solid dose into the human or animal body.

As used herein, the term "transdermal" means the route of administration wherein active ingredients are delivered across the skin for local or systemic distribution.

The "skin" is defined here as a biological membrane, such as the stratum corneum, oral mucosa, ocular membrane, or other mucosal membrane on the surface of the body of the subject, or within a cavity or abdomen of the patient (e.g., applied during surgery).

According to the present invention, there is provided a solid dose for insertion into the skin of a patient wherein the solid dose has a hollow core.

Preferably, the solid dose has a shape which allows delivery of the solid dose into the skin, wherein the shape is conical, frustoconical, cylindrical or a cuboid.

Optionally, the solid dose comprises a proximal end and a distal end, and wherein the distal end of the solid dose is tapered. The solid dose can also be elongated with an aspect ratio of greater than 1.

Preferably, the solid dose comprises at least one active ingredient. Optionally, the solid dose comprises at least one excipient. In accordance with one embodiment, the solid dose consists of an active ingredient.

Preferably, the length of the solid dose is less than 1000 microns. Optionally, the dose is between 10 microns to 20 mm in length.

Optionally, the solid dose is coated with a biodegradable polymer or a carbohydrate. In accordance with the present invention the solid dose can be soluble or biodegradable.

In accordance with a further aspect of the present invention, there is provided a solid dose carrier for the skin insertion of a solid dose as defined herein, wherein the solid dose carrier comprises a proximal portion and a distal portion, wherein the solid dose can be seated on or around the distal portion of the carrier, and wherein the distal portion of the carrier is capable of penetrating the surface of the skin to allow insertion of the solid dose in to the skin.

In one embodiment, the carrier further comprises an insertion mechanism to assist with insertion of the solid dose, wherein the insertion mechanism is adapted to move relative to the carrier and so act to provide resistance to the movement of the solid dose away from the skin as the carrier is pushed into the skin. Optionally, the insertion mechanism is a sleeve which is either partially or completely wrapped around the carrier.

Preferably, the proximal portion of the carrier has a cylindrical shape and the distal portion is capable of penetrating the skin. More preferably wherein the solid dose carrier is a needle.

Optionally, the solid dose carrier is capable of delivering single or multiple doses either consecutively or simultaneously.

Preferably, the solid dose carrier further comprises a solid dose which is seated on or around the distal portion of the carrier.

In accordance with a further aspect of the present invention, there is provided a device for the skin insertion of a solid dose, wherein the device comprises a solid dose carrier as defined herein.

Preferably, the device according to the present invention comprises a lower portion comprising the solid dose carrier and further comprises an upper portion to allow the user to press the device into the skin. The lower portion of the device can also comprise a platform, wherein the solid dose carrier is connected to the platform, and wherein the platform is intended to define the maximum depth of penetration of the solid dose carrier into the skin.

In one embodiment, the device further comprises an outer case comprising one or more cavities, and the upper portion of the device further comprises one or more protrusions, wherein the cavities receive the protrusions to provide resistance to the movement of the device as it is pushed into the skin. Optionally, the outer case further comprises a bottom rib which sits against the skin and provides a means to fix the pressure that is applied to the device to ensure insertion.

In a further embodiment, the device comprises one or more solid dose carriers carrying one or more solid doses. In another embodiment the device is a single use disposable unit.

In accordance with a further aspect of the present invention, there is provided a method of manufacturing a solid dose as defined herein comprising the following steps:
 (i) providing the solid dose ingredients; and
 (ii) shaping the solid dose.

Preferably, the shaping step involves using a method selected from wet casting, direct compression molding or extrusion. Optionally, the shaping step involves compression molding using a multipart tool. The method can also comprise a step of forming a hollow core of the solid dose.

Optionally, the method further comprises the steps of
 (i) placing the solid dose Ingredients into a multipart die;
 (ii) pressing a punch section comprising a pin into the die section to form the hollow core of the solid dose;
 (iii) optionally rotating either the pin or the die muitiparts; and
 (iv) ejecting the formed solid dose from the die, In accordance with another aspect of the present invention, there is provided a further method of manufacturing a solid dose as defined herein comprising the following steps:

(i) coating the solid dose carrier with a lubricant;
 (ii) coating the solid dose carrier with the dose ingredients which are in the form of a liquid, paste or mixture; and
 (iii) drying the coating to form the solid dose.

In a further aspect of the present invention, there is provided a method of delivering a solid dose transdermally to a human or animal using the device as defined herein comprising the steps of:
 (i) pressing the carrier carrying the at least one solid dose into the skin of the human or animal;
 (ii) pushing the carrier and solid dose into the skin to a desired depth; and
 (iii) withdrawing the carrier to leave the solid dose in the human or animal.

Optionally, multiple solid doses are delivered consecutively or simultaneously using the carrier.

A solid dose of this form allows skin insertion without the tip of the solid dose requiring so any specific restrictions to the angle or sharpness to pierce the skin nor the mechanical strength to withstand the compressive forces it will experience when pressed into the skin. Solid doses directly inserted into the skin, relying on their own inherent tip sharpness are liable to break at the tip leading to a blunt tip resulting in significant trauma on the skin and to the patient and also creates potential for poor and inaccurate dosing.

A major benefit of this type of solid dose is that the hollow core is less likely to experience rapid bio-fouling, as would be experienced on the surface of the solid dose, (and as is experienced for needle like glucose sensors that are used for continuous glucose monitoring whereby drift is observed due to the bio-fouling effect), leading to further refinement over the consistency of drug release where a sustained release profile is desired over days or weeks for example.

The skilled person would understand the term "solid dose" to describe a pharmaceutical dosage form. More specifically this term is used to describe a dose that is formed as a mass that is predominantly solid which comprises one or more active ingredients but may also contain excipients such as solvents that act as binding agents, solubility enhancing agents, permeation enhancing agents and other liquids that may be required to achieve the desired rapid or sustained release profile. The solid dose may be composed of a wide range of excipients that are established and documented for tablet manufacture by direct compression, granulation, or micro-molding and micro-replication techniques.

By the term "active ingredient" we mean a biologically active substance that has a therapeutic or cosmetic effect. Biologically active substances can include small molecules, proteins and peptides. In particular, the active ingredient can be selected from, but not limited to vaccines, cosmetic agents (such as Botulinum Toxin), pain-relief drugs (such as opioid analgesics, triptans and NSAID's), hormones (such as Human growth hormone or hydrocortisone), vitamins, anesthetics, antihypertensive agents and contraceptive agents.

To produce solid doses of the desired shape, wet casting techniques may be used. In particular, a suitable mold may be used followed by drying the wet mass, or by extruding as a hollow cylinder followed by cutting to the requisite length. One benefit of using wet molding or extrusion is that upon drying, the solid mass will undergo a certain amount of shrinkage, which will be consistent for a given set of processing conditions and formulation composition, thus reducing the need for high precision tooling with fine tolerances, since a slightly larger solid dose may be prepared and a controlled shrinkage will lead to a smaller dose size on drying.

The solid dose may be any size which is suitable for delivery by the solid dose carrier, and so if, for example, the solid dose carrier is a needle, the solid dose will be restricted by the size of the needle. The size is also restricted by the physical limitation imposed by methods used to produce the solid dose that will enable the solid dose to retain its mechanical properties; this may be in the region of 0.1 mm solid dose wall thickness. In some embodiments, the solid dose may have a size of less than 1000 microns, or preferably between about 10 microns to about 20 mm in length. Preferably, the solid dose is in the form of a pellet.

If the dosage of active ingredient to be administered to a patient is too large, then it can be administered as multiple solid doses, and if required over multiple solid dose carriers.

In some instances of the present invention, the smallest size solid dose may in fact be produced using a completely different process than the casting or extrusion techniques which have been described above.

An alternative method for forming a solid dose can be described using the following steps:
(i) coating the solid dose carrier with a lubricant;
(ii) coating the solid dose carrier with the dose ingredients which are in the form of a liquid, paste or mixture; and
(iii) drying the coating to form the solid dose.

The purpose of the lubricant in the above described method is to prevent the solid dose from sticking to the solid dose carrier. The lubricants which can be used are described below. The coating can be air dried or by using hot air drying techniques.

When using the above method, a shroud is formed around the solid dose carrier that is solidified. The shroud preferably has a thickness of from 10 to 20 um. However, the shroud can be far thinner and smaller than the solid doses which are produced using the direct compression technique. The major advantage of this technique is that very thin solid doses can be produced.

In accordance with the present invention, the lubricants, anti-adherants and glidants that can be used are well known to the skilled person working in the field of formulations and tableting. Examples of lubricants include, but are not limited tool based lubricants such as mineral oils, powder lubricants and glidants. Preferably, the lubricant is selected from one or more of magnesium stearate, calcium stearate, stearic acid, hydrogenated vegetable oil (for example Sterotex®, Lubritab® and Cutina®), mineral oil, polyethylene glycol (for example PEG 4000-6000), sodium lauryl sulfate, glyceryl palmitostearate (Precirol®), glyceryl behenate (Compitrol 888 ®) and sodium stearyl fumarate.

Preferably the anti-adherant and glidant is selected from talc or fumed silicon dioxide.

The solid dose may also be composed of drug alone where the drug is a solid with the appropriate properties for being converted into a solid dose with a hollow core. The shape of the solid dose may include a hollow cone, a hollow cylinder, a hollow sphere, hollow rectangle, hollow frustoconical, hollow cuboid or indeed any shape with one or more faces. It may be preferable that where the solid dose is large, e.g., for administration to animals where the dose may be several millimeters in length. Additionally the dose may be elongated, i.e., to have an aspect ratio greater than 1. The solid dose in accordance with the present invention may contain a leading edge (that will first enter the skin) that does not contain any sharp corners, but instead may have a rounded edge or an irregular shaped edge.

As used herein, the term "hollow" is used to mean a cavity which extends from the proximal end towards the distal end of the solid dose. The cavity can extend partly or completely from the proximal end to the distal end of the solid dose. Preferably, the hollow core extends completely from the proximal end to the distal end of the solid dose.

The objective of the present invention is to prevent the leading edge from providing large frictional forces or obstruction to the entry of the solid dose. The size of the solid dose may vary from sub-millimeter to over 10 mm. Preferably wherein the diameter of the solid dose is from 10 microns to about 20 mm, or about 0.01 mm to 15 mm, more preferably from 0.5 mm to 10 mm, and still more preferably from 1 min to 5 mm. In one embodiment, the solid dose has a conical shape and is hollow. Preferably the solid dose has an outer width at the top of the cone of 0.5 mm, and a length of 0.5 mm. The sub-millimeter solid dose is preferably prepared using micro-molding techniques widely employed for microneedle production, and the larger sized solid dose is preferably prepared using more conventional compression techniques.

For the manufacture process of the solid dose, where compression or pressure molding techniques are used, it would be preferable that a multipart tool is used In particular for solid doses with dimensions in the sub-7-8 mm length range. It has been found that solid doses of this size range and lower are difficult to remove from the mold tooling. In the event where the mold tooling is electro polished on the interior surface, the reduction in friction rapidly wears off and the solid doses cannot be readily ejected from the tool.

Additionally a pin can be used to form the hollow core of the solid dose. It has also been demonstrated that rotation of the mold cavity and/or the pin (in opposing directions) during compression, further facilitates the formation of a solid dose with smooth surface properties, and is readily ejected from the tool after its formation by compression.

Furthermore enhanced mechanical properties are achieved due to better compaction when the solid mass for the solid dose is placed into the (multipart) die prior to the die completely closing up to form the desired cavity. The punch section with a pin is then pressed into the die section simultaneously as the die section closes to form the solid dose wall cavity; the die multi-parts may also be rotating as they close to form the cavity for the solid dose.

A further embodiment of the invention is whereby the solid dose is coated with a biodegradable polymer, carbohydrate or other material that provides a high level of toughness and resistance to compressive forces and any resistance that may be experienced as the dose passes through the skin. Types of tablet coatings would be well known to the skilled person and can include sugar coatings and film coatings. Such coatings are already practiced in the drug tableting field whereby the coating either reduces the friability of a tablet or imparts controlled or sustained release properties to the tablet; the same principle can be applied to the present invention.

In accordance with a further embodiment of the present invention, to prevent the breakage of the leading regions, the solid dose may be tapered, thus thinner) towards the distal end (otherwise known as the leading end which is the portion of the solid dose that first enters the skin). The solid dose may be tapered to less than 50 microns, and more preferably less than 10 microns.

The solid dose may be inserted into the skin after the entry of the protruding portion of the carrier, with resistance to movement of the solid dose further up the carrier provided by a flat edge against which the proximal portion of the solid dose rests on the carrier. It may also be further pushed into the skin if desired using an insertion mechanism which may be a sleeve around the carrier which is able to move relative to the carrier, where the sleeve may be partially or completely wrapped around the carrier. In this case the sleeve would act to provide the resistance to movement of the solid dose away from the skin as the carrier is pushed into the skin.

The solid dose carrier may be an injection device that is predominantly cylindrical in shape such as a needle, with a leading tip, that may be pointed or flat, that has the requisite sharpness to penetrate the skin. The carrier may also have a flat wall, such as a lancet, or some combination of wall contours that provide the requisite physical dimensions to enable a hollow solid dose to be positioned over the carrier for the purposes of being inserted into the skin of a human or animal. A single or multiple solid doses may be delivered from a single device, in a single motion, consecutively or simultaneously as required, i.e., the device may have one or more carrier.

According to the present invention, the solid dose carrier can be from about 0.1 mm to about 1 mm in diameter. In some embodiments, the carrier can have a diameter of greater than >1 mm diameter e.g., for animal vaccines it could be 2-3 mm diameter. The carrier from which the carrier comprises can include a metal (e.g stainless steel. Alternatively the carrier can be comprised of a ceramic or polymer material.

As the person skilled in the art will appreciate, the force which is required by the clinician, or even the patient themselves, to push the solid dose carrier with the solid dose into the skin is dependent upon the size of the solid dose carrier and the size of the solid dose.

The larger the solid dose, the larger the forces will be required (for example >20N). When smaller solid doses are carried on a smaller carrier, then generally smaller forces are required. In the case of a <0.1 mm needle with a 0.1 mm shroud thickness the force is <5N. However, other factors can also influence the force to be applied such as the skin thickness and roughness of the human or animal patient. So with very rough and textured skin the force may be increased several fold. However, the present invention does not require the very large forces which are essential for direct insertion of the pointed or shaped solid doses known in the art (such as those described in US 2011/0313348).

Figure 1:
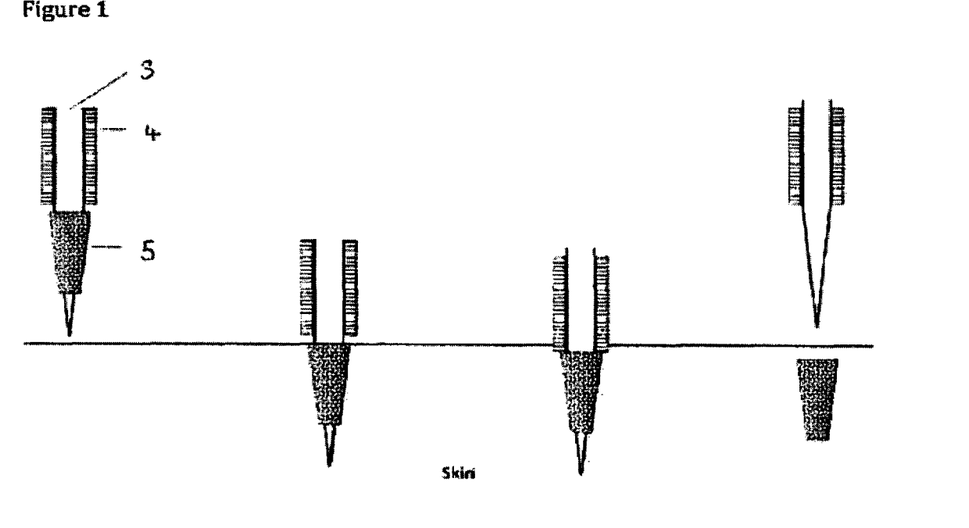
FIG. 1—Schematic of the device and solid dose delivery process.

The device (20) according to the present invention is shown in FIG. 1 in use and illustrates the solid dose delivery process. A solid dose carrier (3) is shown as carrying the solid dose (5) and a sleeve (4) (indicated as an insertion rod) is shown shrouding the upper proximal portion of the carrier, and the solid drug pellet shown shrouding the distal portion of the carrier, with a sharp tip from the carrier protruding out from the base of the solid drug pellet. This is then shown inserted inside the skin followed by further insertion of the solid dose using the sleeve, and retraction of the device with the solid dose remaining inside the skin. Protrusion of the tip of the carrier may be tens to several thousand micrometers, preferably 10 to 5,000 micrometers, more preferably 20 to 2,000 micrometers and more preferably 50 to 1,000 micrometers.

The depth of insertion is dependent upon the size of the solid dose. In one aspect wherein the dose is a large dose of approximately >1 mm in length, then the solid dose will be required to be pushed deeper into the skin, than if it is a smaller solid dose, of approximately <1 mm length. The depth is determined such that it is sufficient to ensure the pellet does not protrude back out of the skin. In accordance with the present invention, the solid dose is pushed to a depth of at least 0.5 mm into the skin, preferably the solid dose is pushed to a depth of about 0.5 mm to about 1 mm.

Figure 2:
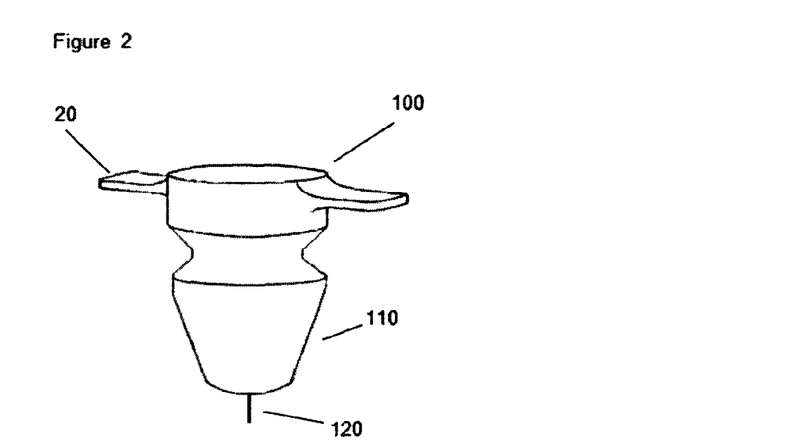
FIG. 2—Illustration of the device indicating an upper portion for pressing down with palm, and lower portion with a needle indicated as the carrier of the solid dose (solid dose not shown).

In FIG. 2, the device of the present invention is shown with an upper surface (100) for pressing down with the palm, and lower portion (110) with a needle (120) indicated as the carrier of the solid dose (solid dose not shown). The device (20) is shown as a single use disposable component without any moving parts whereby a single motion of pushing the carrier/solid dose into the skin leads to delivery of the solid dose into the skin to a pre-defined depth.

Figure 3:
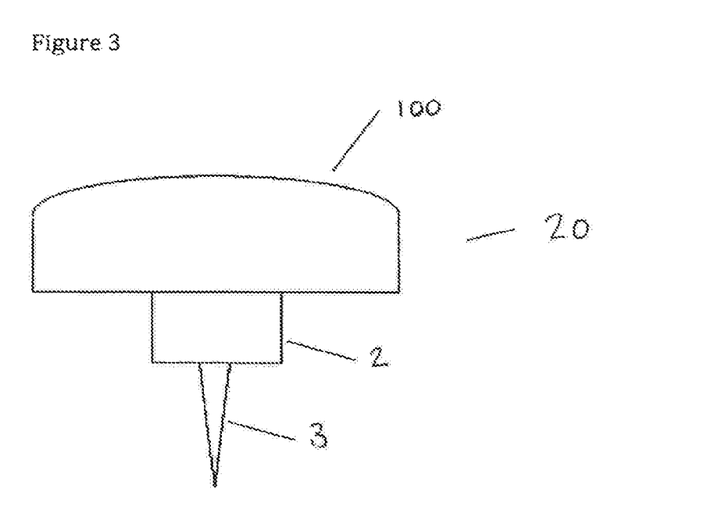
FIG. 3—Schematic representation of the device.

In FIG. 3, the device (20) of the present Invention is shown having an upper surface (100) which is used to apply the device by applying manual pressure to this portion. The carrier (3) with a sharp tip is shown attached to a platform (2) which is intended to define the maximum depth of penetration of the solid dose carrier.

Figure 4:
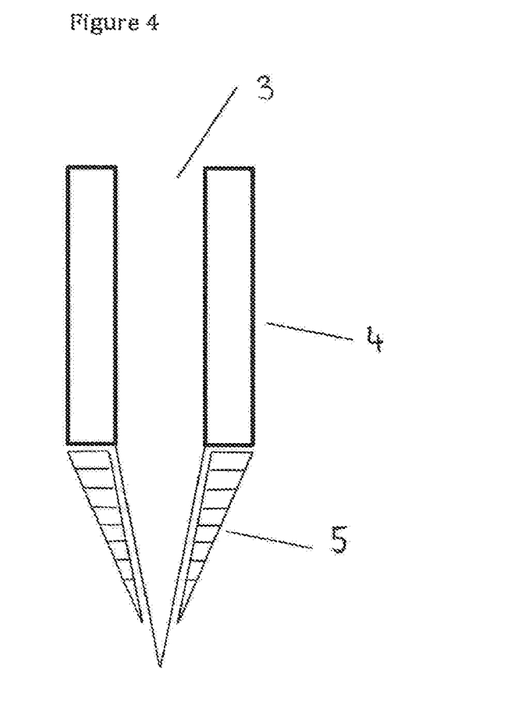
FIG. 4—Cross section of the carrier portion of the device.

In FIG. 4 the cross-section of the carrier portion of the device is shown with the carrier (3), solid dose insertion sleeve (movable relative to the carrier) or restraint sleeve (fixed position relative to the carrier) (4) and solid dose (5) shown as a hollow conical dose.

Figure 5:
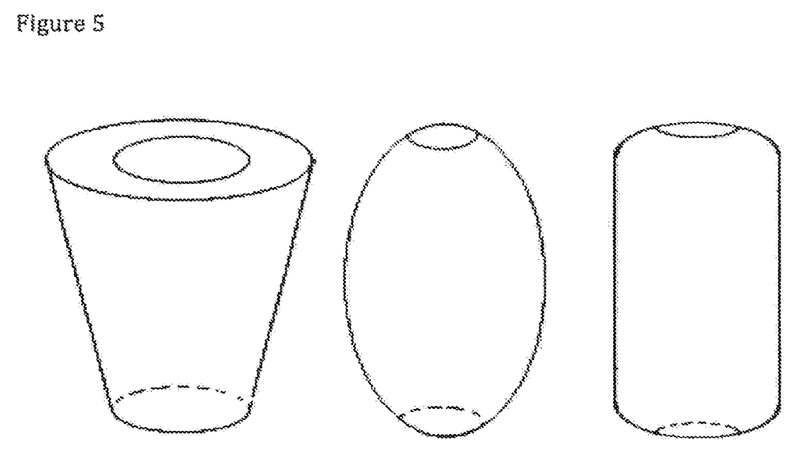
FIG. 5—Schematic representation of various shapes of the solid dose.

FIG. 5 illustrates that the solid dose can comprise of various shapes and dimensions which include, but are not limited to the shape of a hollow cone, hollow cocoon and hollow rectangular shape with smoothed edge profile. It will be appreciated that these are mere representations of the shapes and dimensions of the solid dose that can be produced and is not intended to be an all-encompassing representation.

Figure 6:
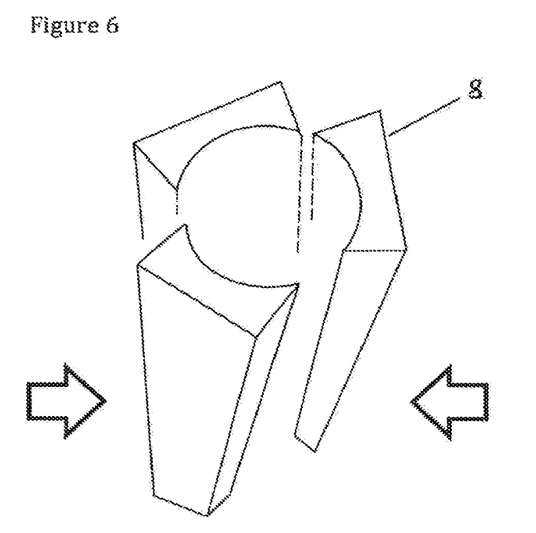
FIG. 6—Schematic illustration of a three-part mold tool for producing the solid dose.

The three-part mold tool for producing the solid dose is shown in FIG. 6, with each of the three parts (8) shown in the open position, with the block arrows intended to indicate the movement of the parts together. After compression the three parts are moved apart leading to the dose being readily ejected from the die. It will be appreciated that the three-part tool is a representation of a multi-part tool system, and the tooling may contain one or more parts for the die section according to the needs based on the solid dose size and geometry, Release agents may be used to assist in removing the formed solid dose from the die. A suitable release agent is magnesium stearate.

Figure 7:
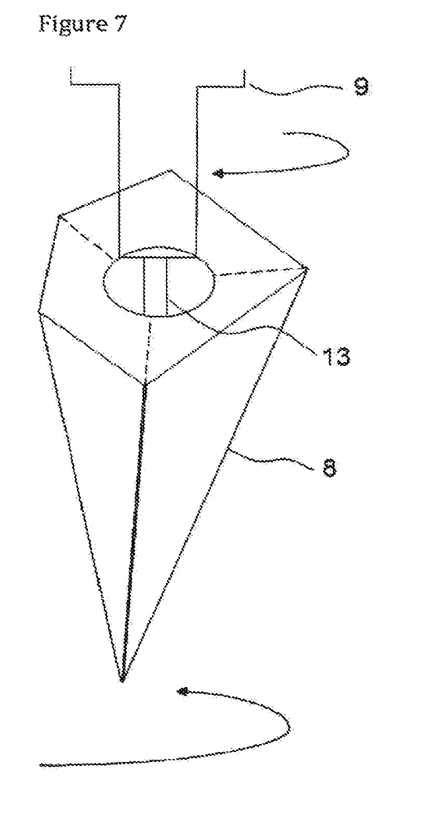
FIG. 7—Schematic illustration of the mold tool and pin associated with the compression die.

FIG. 7 shows a multi-part mold tool die (8) and punch (9), and pin (13) which can be used to prepare the solid dose of the present invention. The arrow shown next to the punch is intended to indicate the punch rotating as well as moving down vertically to compact the mass into a solid dose. The arrow indicated next to the die section is intended to indicate the rotation of the die before. This rotation may be during and possibly after the die section has closed together to form the desired cavity.

Figure 8:
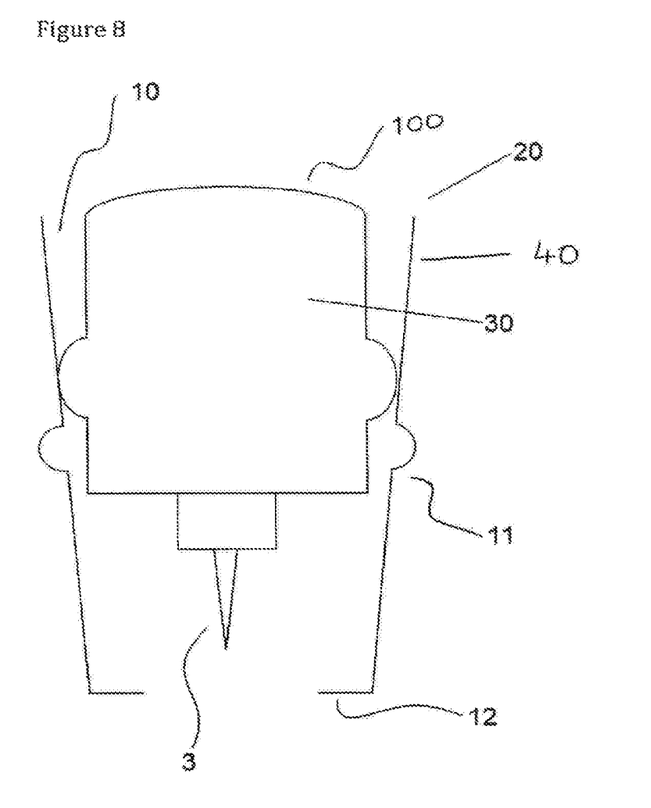
FIG. 8—Schematic illustration of the device within an outer case which provides resistance to the movement of the solid dose/carrier.

The device (20) is shown in FIG. 8 within an outer case (40) which provides resistance to the movement of the solid dose/carrier. The upper surface (100) of the main body (30) of the device (20) is shown at an elevated position relative to the outer case (40). The body (30) of the device is also shown with protrusions (10) on the surface to provide resistance to movement of the device as it is pushed into the skin. The body (30) of the device can comprise one or more protrusions (10). The outer case (40) has a corresponding cavity in the case wall (11) which will seat the protrusion(s) (10) on the main device housing once the latter has been depressed far enough. The outer casing (40) is shown with a bottom rib (12) which seats against the skin.

This embodiment of the device provides a means to fix the pressure that is applied to the device to ensure insertion. By designing the one or more protrusions (10) on the main device body (30), and flexibility into the outer case (40) such that for the drug carrier (3) to move down and into the skin a defined force must be applied to overcome the resistance from the protrusion to enable the inner main device body (30) to move relative to the outer case (40).

An added benefit of this is that once the force threshold has been reached the carrier (3) and solid dose (5) will rapidly enter the skin thus avoiding the possibility of an operator mis-dosing due to inadequate penetration of the solid dose into the skin. This also provides a means of ensuring the same device cannot be used twice on a patient, by ensuring the outer and inner case lock together at this point of insertion.

The present invention provides an enlarged surface area through a combination of the surface and the inner walls of the hollow core of the dosage, into which fluid from the skin will diffuse and provide rapid dissolution where desired, depending on the formulation of the dose. The larger surface area from which gradual erosion can occur provides a greater degree of control over the controlled or sustained release from the solid dose by virtue of the surface area to volume ratio i.e., the variability of release profile for a given surface area will be reduced with an increase in surface area.

Figure 9:
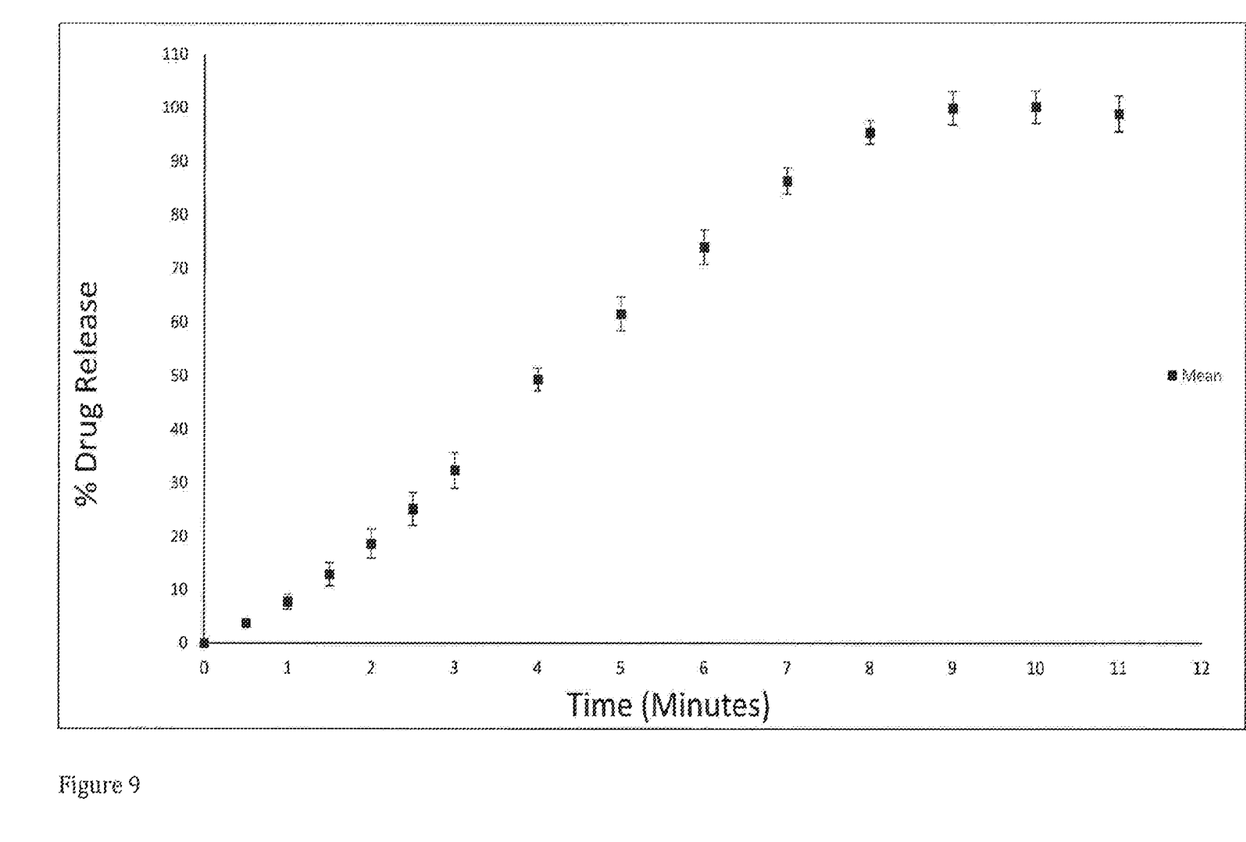
FIG. 9—A graph showing the release of diclofenac sodium in a pellet, formed according to the present invention, wherein the pellet comprises 40% diclofenac sodium and 60% sucrose.

As the skilled person will appreciate there are a wide range of formulations known in this particular field that provide a dynamic range over which drug release occurs. The dose may be delivered for localised drug delivery to the extent that it does not release fast enough for systemic absorption, or it may be released within tens of seconds (as demonstrated by recent dissolution studies illustrated in FIG. 9) for rapid systemic absorption.

EXAMPLE

A typical solid dose prepared according to the present invention contains the following ingredients:

Formulation A: Microcrystalline cellulose as key bulking agent (80% by weight), and 20% Bovine Serum Albumin, (up to 20% by weight).

The above formulation was also prepared using Pearlitol (direct compression mannitol) and sodium carboxy methyl cellulose in replacement of microcrystalline cellulose.

It was found that for the above tested formulations, the compressed solid dose mechanical properties were acceptable for skin insertion.

The invention claimed is:

1. A solid dose for insertion into the skin of a patient wherein the solid dose is a pellet having a hollow core, wherein the solid dose comprises a proximal end and a distal end, wherein the hollow core extends completely from the proximal end to the distal end of the solid dose, wherein the solid dose is configured to be seated around a carrier, wherein the proximal end of the solid dose detachably rests on the carrier, wherein the carrier is capable of penetrating the surface of the skin of a patient to allow for the solid dose to be delivered instantly without the need for any residence time of the carrier inside the skin once the solid dose has been inserted; and wherein the solid dose is configured to remain substantially undissolved upon retraction of the carrier.

2. The solid dose according to claim 1 wherein the solid dose has a shape which allows delivery of the solid dose into the skin, wherein the shape is conical, frustoconical, cylindrical or a cuboid.

3. The solid dose according to claim 1 wherein the distal end of the solid dose is tapered.

4. The solid dose according to claim 1 wherein the solid dose is elongated with an aspect ratio of greater than 1.

5. The solid dose according to claim 1 wherein the solid dose comprises at least one active ingredient.

6. The solid dose according to claim 1 wherein the solid dose comprises at least one excipient.

7. The solid dose according to claim 1 wherein the solid dose consists of an active ingredient.

8. The solid dose according to claim 1 wherein the length of the solid dose is less than 1000 microns, or wherein the length of the solid dose is between 10 microns to 20 mm in length.

9. The solid dose according to claim 1 wherein the solid dose is coated with a biodegradable polymer or a carbohydrate.

10. The solid dose according to claim 1 wherein the solid dose is soluble or biodegradable.

11. A method of manufacturing a solid dose as defined in claim 1 comprising the following steps: (i) providing the solid dose ingredients; and (ii) shaping the solid dose.

12. The method according to claim 11 wherein the shaping step involves using a method selected from wet casting, direct compression molding or extrusion.

13. The method according to claim 11 wherein the shaping step involves compression molding using a multipart tool.

14. The method according to claim 13 further comprising a step of forming a hollow core of the solid dose.

15. The method according to claim 14 wherein the method further comprises the steps of (i) placing the solid dose ingredients into a multipart die; (ii) pressing a punch section comprising a pin into the die section to form the hollow core of the solid dose; (iii) optionally rotating either the pin or the die multiparts; and (iv) ejecting the formed solid dose from the die.

* * * * *